(12) United States Patent
Matsutani et al.

(10) Patent No.: US 8,328,832 B2
(45) Date of Patent: Dec. 11, 2012

(54) MEDICAL KNIFE

(75) Inventors: Kanji Matsutani, Utsunomiya (JP); Masahiko Saito, Utsunomiya (JP)

(73) Assignee: Mani, Inc., Utsunomiya, Tochigi (JP)

( * ) Notice: Subject to any disclaimer, the term of this patent is extended or adjusted under 35 U.S.C. 154(b) by 1351 days.

(21) Appl. No.: 11/526,865

(22) Filed: Sep. 26, 2006

(65) Prior Publication Data

US 2007/0179515 A1    Aug. 2, 2007

(30) Foreign Application Priority Data

Sep. 30, 2005 (JP) .................. 2005-287286

(51) Int. Cl.
*A61B 17/32* (2006.01)
(52) U.S. Cl. .................. 606/167; 148/326; 148/905
(58) Field of Classification Search ................ 606/107, 606/166, 167; 148/95, 559, 566, 576, 579, 148/595, 597–599, 605, 607–611, 622, 624, 148/645, 648, 650, 651
See application file for complete search history.

(56) References Cited

U.S. PATENT DOCUMENTS

RE28,964 E * 9/1976 Nunes et al. .................. 148/610
6,554,840 B2 * 4/2003 Matsutani et al. ............ 606/107

FOREIGN PATENT DOCUMENTS

| JP | 59-87988 A | 5/1984 |
| JP | 64-11084 B | 2/1989 |
| JP | 09-276284 | * 10/1997 |

OTHER PUBLICATIONS

JP 09-276284. Inventors: Matsutani et al. (Machine Translation by JPO.).*
Callister, Jr., William D.; Materials Science and Engineering, An Introduction (Sixth edition); John Wiley & Sons, 2003. (pp. 134-140).*

* cited by examiner

*Primary Examiner* — Scott Kastler
*Assistant Examiner* — Vanessa Luk
(74) *Attorney, Agent, or Firm* — Smith Patent Office

(57) ABSTRACT

A work 10 made of a hard wire rod of austenitic stainless steel is pressed at a rolling reduction of 60% or greater, into a paddle-shaped end 10b, and then subjected to work hardening, making the hardness of the end 10b 550 Hv or greater. Afterwards, the paddle-shaped end 10b is cut through machining, forming a main body 10c of a medical knife and cutting blades 10d. As a result, a medical knife, which is easily fabricated, is corrosion resistant, has sufficient hardness and sharpness, high toughness preventing cracks, can be provided.

13 Claims, 4 Drawing Sheets

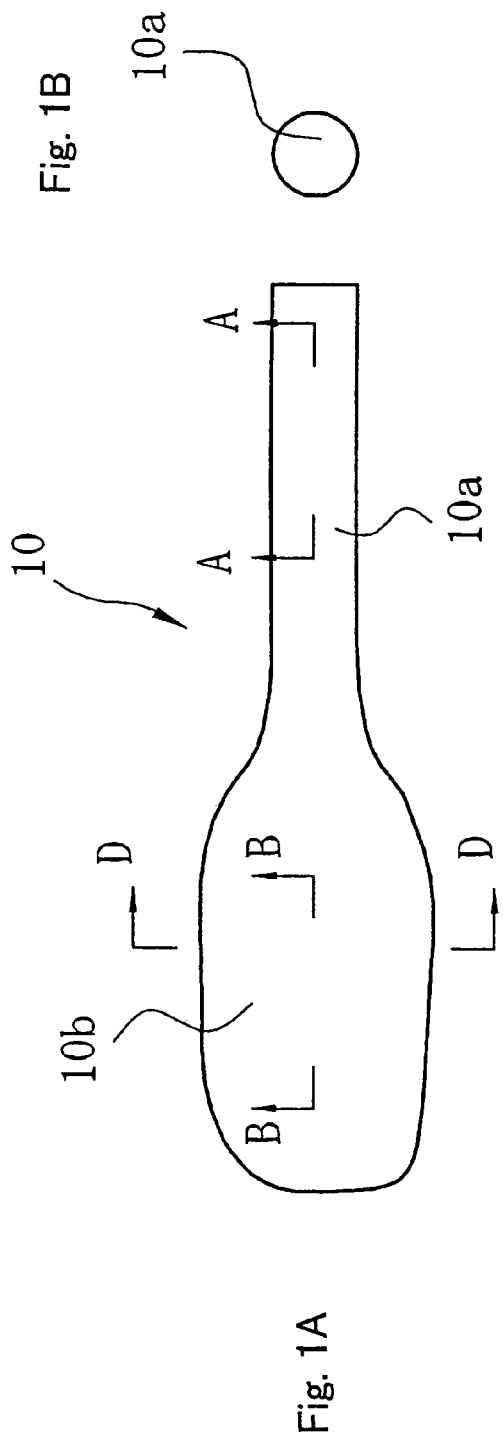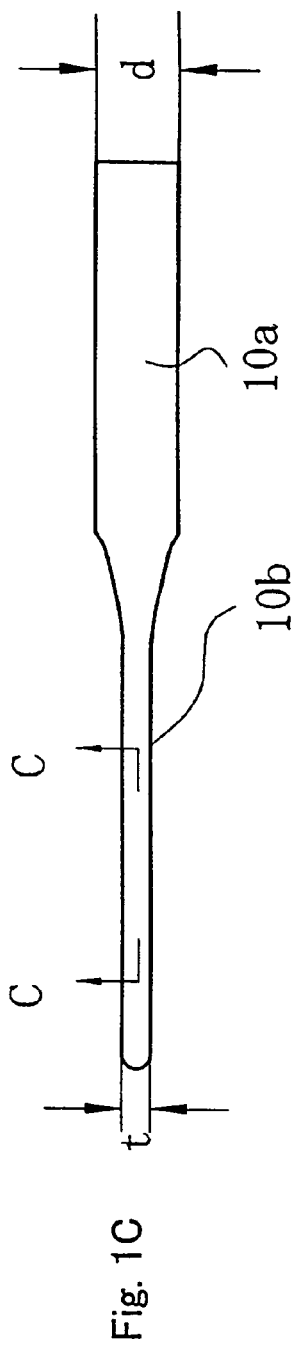

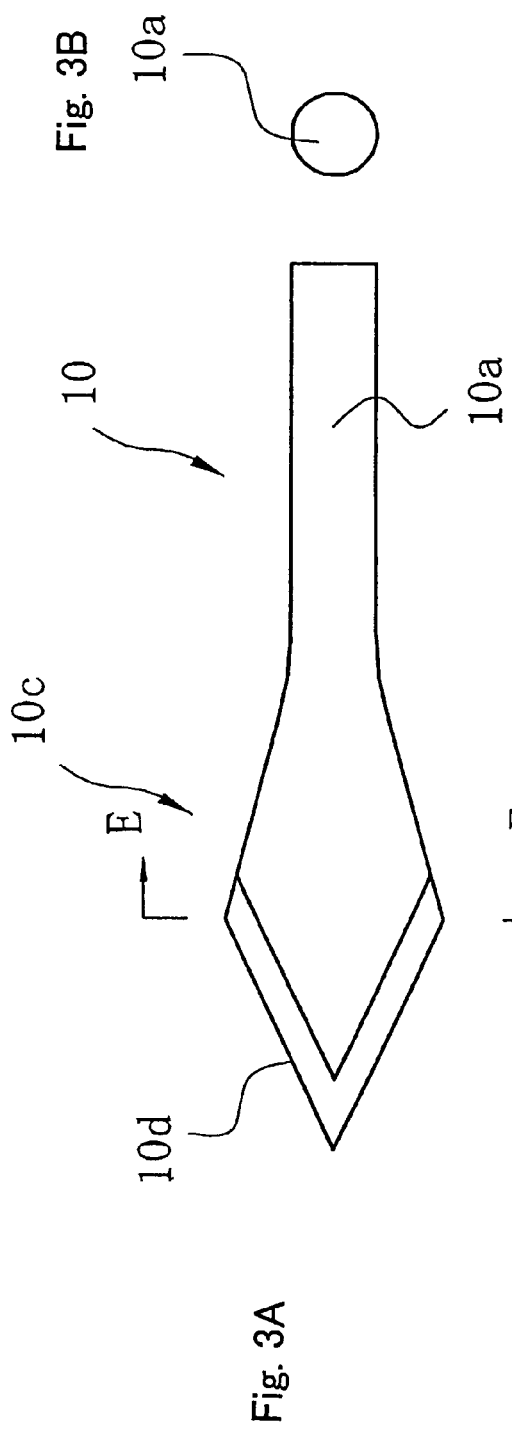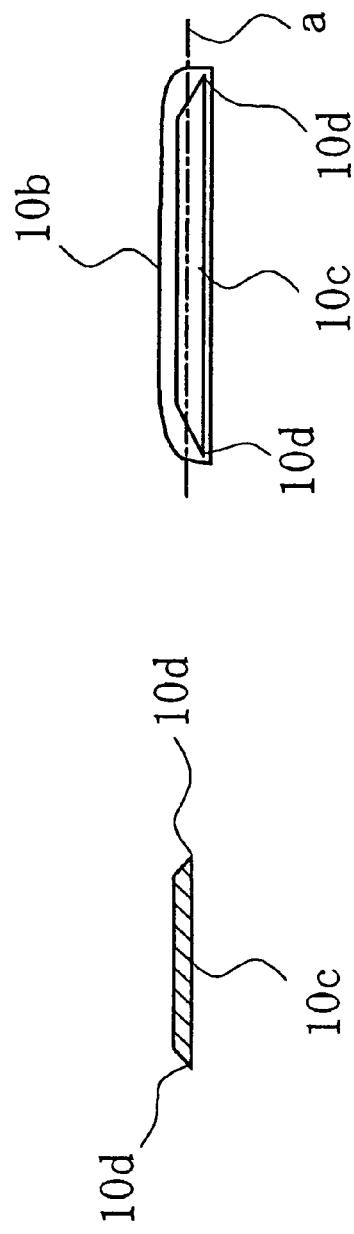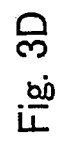

| | HARDNESS (Hv) | ROLLING REDUCTION | EVALUATION BY DOCTORS | | | |
|---|---|---|---|---|---|---|
| | | | DOCTOR A | DOCTOR B | DOCTOR C | DOCTOR D |
| | 450 | 0% | × | × | × | × |
| | 500 | 20% | △ | × | △ | × |
| | 550 | 40% | ○ | △ | △ | × |
| | 600 | 60% | ○ | ○ | ○ | △ |
| | 660 | 75% | ○ | ○ | ○ | ○ |

MEDICAL KNIFE

BACKGROUND OF THE INVENTION

1. Field of the Invention

The present invention relates to a medical knife. In particular, it relates to a medical knife used for microsurgery such as ophthalmic surgery, cerebral surgery, or for surgery of blood vessels, etc.

2. Description of the Related Art

Conventionally, medical knives have been manufactured in the following manner. First, a wire rod of carbon steel, martensitic stainless steel, or precipitation hardened stainless steel 6 to 10 mm in diameter is used as a raw material. In the case of carbon steel and martensitic stainless steel, they are subjected to wire drawing into a wire rod approximately 1 mm in diameter. In the case of stainless steel, it is subjected to solution heat treatment between each wire drawing. The resulting processed wire rod is cut into pieces of an appropriate length, which are then subjected to annealing, press working into a flat shape, grinding to form blades, and quenching, making completed products. In the case of precipitation hardened stainless steel, after repeating wire drawing and solution heat treatment to make it approximately 1 mm in diameter, it is then cut into pieces of a pre-determined length. The pieces are then subjected to press working and grinding without being subjected to annealing, and then subjected to precipitation hardening treatment rather than quenching.

With such a manufacturing method, since wire rods are subjected to annealing before processing, processing is easily performed; however, quenching and precipitation hardening treatment tend to cause a crack, a chip or a break due to lack of toughness. Moreover, rust tends to develop due to the characteristics of the material, causing a problem of low corrosion resistance.

To solve such problems, Examined Japanese patent application laid-open No. Hei 1-11084 proposes a product manufacturing method for wire drawing a wire rod of austenitic stainless steel at a reduction ratio of 80% or greater and subjecting it to predetermined processing while keeping the temperature of the wire rod of steel at approximately 500° C. or less. The temperature of 500° C. or less is set, emanating from the fact that the hardness increased through work hardening decreases at 500° C. or greater. It is impossible for austenitic stainless steel to be subjected to quenching; instead, work hardening due to wire drawing is available. Use of austenitic stainless steel allows improvement in corrosion resistance. Moreover, since quenching is impossible, the problem of a quenching crack or chip cannot occur.

Japanese patent application laid-open No. Sho 59-87988 proposes use of composite stainless steel manufactured by generating a decarburized layer on the surface of martensitic stainless steel with high carbon density and high chromium density and then joining it with austenitic stainless steel. According to this proposal, a blade is formed in the martensitic stainless steel and then subjected to quenching to ensure sufficient sharpness, and high toughness of the austenitic stainless steel prevents a quenching crack or chip at the same time.

Examined Japanese patent application laid-open No. Hei 1-11084 is suitable for suture needles; however, it cannot provide sufficient hardness for necessary sharpness for knives. Meanwhile, the method using composite stainless described in Japanese patent application laid-open No. Sho 59-87988 is suitable for a fabrication of large cutting tools such as household cutting tools; however, it cannot be applied to a fabrication of small knives such as medical knives. In particular, it is very difficult to fabricate medical knives for microsurgery.

SUMMARY OF THE INVENTION

The present invention is devised in light of the aforementioned problems and aims to provide a medical knife that can be easily fabricated, is corrosion resistant, has sufficient hardness and sharpness, and high toughness preventing a crack.

To attain the objective described above, a medical knife according to the present invention is characterized by a flat-shaped end formed by cold pressing a wire rod of austenitic stainless steel with a fibrous structure at a rolling reduction of 60% or greater; and a cutting blade formed in a region of the end; wherein the fibrous structure includes grains having a cross section long along the width of the cutting blade of the end and short along the thickness thereof; and as compared to the density of a cross section of the fibrous structure along the length of the wire rod before cold pressing, density of a cross section of the fibrous structure along the length of the end perpendicular to the flat-shaped surface of the end is higher, and density of a cross section of the fibrous structure along the length of the end parallel to the flat-shaped surface of the end is lower, and hardness of the end is 550 Hv or greater, provided through work hardening.

The medical knife herein includes those for microsurgery such as ophthalmic surgery, cerebral surgery, surgery of blood vessels or the like in addition to medical knives used for general surgical operations.

The positions of the cutting blades are preferably away from the center area of the material. Further, it is preferable to use a material having a value close to the upper limit or over the upper limit of tensile strength specified in type-B stainless steel SUS302 for springs (JIS G4314) as an example of a hard wire rod of austenitic stainless steel. Furthermore, another example may be a wire rod with grains comprising a long and thin fibrous structure made by wire drawing a wire rod of austenitic stainless steel several times. Moreover, it is preferable that such several times of wire drawing be executed such that solution heat treatment is executed before each wire drawing, namely executing solution heat treatment, wire drawing, solution heat treatment, wire drawing, solution heat treatment, in this written order, for example. The austenitic stainless steel is preferable to have a carbon content of 0.08% to 0.15%.

A hard wire rod of austenitic stainless steel is cut into pieces or works of a predetermined length, and the end of each work is then pressed into a flat shape through press working. In the case of rolling reduction of 60% or greater, work hardening occurs, thereby reaching a vickers hardness of 550 Hv or greater. A medical knife is formed by grinding this material with a grindstone or the like and then forming a cutting blade.

Note that a medical knife having a flat shaped blade can be formed through cold pressing a wire rod with a fibrous structure at a rolling reduction of 60% or greater; for example, a medical knife used to cut a cornea or a sclera in ophthalmic surgery can be formed preferably. The structure is pressed horizontally and thus extended vertically. As a result, grains having a cross section long along the width of the cutting blade of medical knife and short along the thickness thereof are formed. According to observation of the size of each grain, it is approximately 0 to 2 μm along the thickness thereof while it is approximately 30 to 40 μm along the width of the blade. Moreover, according to observation of the density of the fibrous structure, the density of a cross section of the fibrous structure along the length thereof perpendicular to the flat-shaped surface formed by cold pressing is twice that of a cross section of the fibrous structure cut along the length thereof before press working, and density of a cross section of the fibrous structure cut along the length thereof parallel to the flat-shaped surface is 0.5 times or less.

Furthermore, while the main body of the medical knife is formed by cold pressing the end of a work into a paddle-shaped end and then grinding it with a grindstone or the like, it may be formed by press cutting a paddle-shaped portion into a main body of a medical knife and then grinding it, forming cutting blades. In the case of use of press cutting, hardness can be further increased because cutting causes work hardening again. Furthermore, sharper cutting blades can be formed by being subjected to electrolytic polishing or chemical polishing after grinding with a grindstone.

Yet furthermore, cutting blades of a medical knife should be formed at positions away from the center of a paddle-shaped end, which is formed by cold pressing the end of a work, along the thickness thereof. This is because the center area along the thickness has low hardness and includes a lot of impurities. Since electrolytic polishing and chemical polishing cause areas including a lot of impurities to be etched in a concentrated manner at first, formation of a cutting blade at the center along the thickness may cause the blade to chip and become rough.

Since the medical knife according to the present invention is made of austenitic stainless steel, it has excellent corrosion resistance, thus is hard to rust. Moreover, since it has hardness of 550 Hv or greater, it has sufficient hardness and sharpness for medical use, and can be easily fabricated. Moreover, a very small medical knife for microsurgery can be easily fabricated from a thin wire 1 mm in diameter.

BRIEF DESCRIPTION OF THE DRAWINGS

FIG. 1A is a plan view of a work fabricated by cutting a round wire rod of stainless steel into pieces and then press working the end of each piece into a flat shape;

FIG. 1B shows the shape of the right end surface of the work in FIG. 1A;

FIG. 1C shows the shape of the bottom surface of the work in FIG. 1A;

FIG. 1D is a cross section of the work in FIG. 10 cut along a line D-D;

FIG. 3A is a plan view of a work with a cutting blade;

FIG. 3B shows the shape of the right end surface of the work in FIG. 3A;

FIG. 3C shows a cross section of the work in FIG. 3A cut along a line E-E;

FIG. 3D is an enlarged view showing that the end of the work is carved into a main body of a medical knife;

DETAILED DESCRIPTION OF THE PREFERRED EMBODIMENT

Figure 2A:
FIG. 2A is a picture of a cross section of a metallic structure of the work in FIG. 1A cut along a line A-A.

An embodiment according to the present invention is described forthwith with reference to attached drawings.

Austenitic stainless steel SUS302 (carbon content: 0.15% or less) is used as the material for a medical knife according to the present invention. This type-B stainless steel SUS302 for springs or SUS304 having less carbon content may be used. The carbon content included in the SUS304 is 0.08% or less. However, since the carbon content greatly influences work hardening, the carbon content of the SUS304 is considered to be the lower limit, namely, approximately 0.08% to 0.15%.

Once a wire rod of SUS302 6 to 10 mm in diameter is subjected to solution heat treatment, the resulting wire rod is wire-drawn into 5 to 8 mm in diameter (reduction ratio is approximately 60%). This is subjected to solution heat treatment again, then wire-drawn into 2 to 3 mm in diameter (reduction ratio is approximately 60%). This is further subjected to solution heat treatment again, then wire-drawn into approximately 1 mm in diameter (reduction ratio is approximately 70%).

Such solution heat treatment is required to change carbide, which is generated when a wire rod of austenitic stainless steel is wire-drawn through cold working, to solid solution, and to remove internal stress so as for the wire rod to be softer, allowing it to be wire-drawn and recovery of ductility. In general, it is heated up to 1010 to 1150° C. and held awhile, and then rapidly cooled.

The reduction ratio is represented by the following equation where D1 denotes a diameter before processing and D2 denotes a diameter after processing.

$$\text{Reduction ratio (\%)}=(D1^2-D2^2)/D1^2\times100\%$$

Changes in the metallic structure due to the above-mentioned wire-drawing are described forthwith. The first metallic structure of the wire rod 6 to 10 mm in diameter is of austenite; however, repetition of wire-drawing reduces the austenitic structure, increasing the martensitic structure instead. When it finally becomes approximately 1 mm indiameter, it includes thin and long crystals looking like fibers with 50% or less austenitic structure content and 50% or more martensitic structure content. As the martensitic structure increases, tensile strength also increases. With a fibrous structure, tensile strength can be increased up to approximately 2400 N/mm².

The wire rod prepared in such a manner is cut into a predetermined length, and an end thereof is then pressed into a flat shape through press working.

FIGS. 1A to 1D show a work fabricated by cutting a round wire rod of stainless steel and pressing an end thereof into a flat shape through press working. FIG. 1A shows a plan view of a work, FIG. 1B shows an end surface thereof, FIG. 1C shows the bottom surface thereof, and FIG. 1D shows a cross section cut along a line D-D in FIG. 10. As shown in these drawings, a work 10 has a shape having a round wire rod shaped base 10a continuously followed by a paddle-shaped end 10b provided through press working.

Figure 2B:
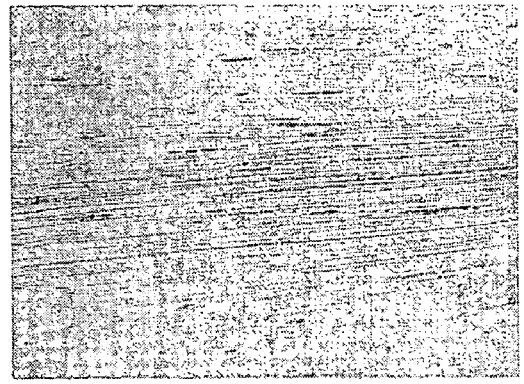
FIG. 2B is a picture of a cross section of the metallic structure of the work in FIG. 1A cut along a line B-B.
Figure 2C:
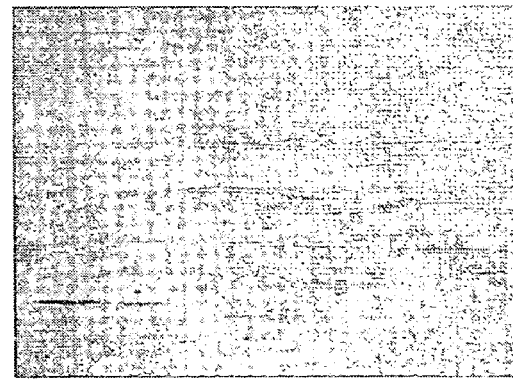
FIG. 2C is a picture of a cross section of the metallic structure of the work in FIG. 1A cut along a line C-C.
Figure 2D:
FIG. 2D is a picture of a cross section of the metallic structure of the work in FIG. 1A cut along a line D-D.

FIGS. 2A to 2D are pictures of a metallic structure of the work 10 provided through press working as described above. FIG. 2A is a picture of a cross section of the round wire rod of the work along the length thereof cut along a line A-A in FIG. 1, taken by an electron microscope. FIG. 2B is a picture of a cross section of the metallic structure of the work cut along a line B-B in FIG. 1, or cut along a line perpendicular to the flat surface of the paddle-shaped end along the length thereof, taken by an electron microscope. FIG. 2C is a picture of a cross section of the metallic structure of the work cut along a line C-C in FIG. 1, or cut along a line parallel to the flat surface of the paddle-shaped end along the length thereof, taken by an electron microscope. FIG. 2D is a picture of a cross section of the metallic structure of the work cut along a line D-D in FIG. 1, or a cross section of the paddle-shaped end, taken by an electron microscope.

For taking a picture of such a metallic structure, a surface to be observed is etched. There are two methods for etching such a surface: one etching method that uses aqua regia and another method that is based on galvanic corrosion. According to this embodiment, since a picture of grains developed through galvanic corrosion is taken clearer, observations of the respective cross sections, cut and subjected to galvanic corrosion treatment, through an electron microscope are shown in FIGS. 2A to 2D. Black portions in these pictures are impurities. With this embodiment, grain boundaries of grains are unclear in the pictures due to use of quality stainless steel.

FIG. 2A shows that the shape of the grains comprises a long and thin fibrous structure due to the above-mentioned wire drawing. This portion has predetermined hardness (about 450 Hv). Furthermore, impurities concentrate at the center along the thickness thereof. FIG. 2B shows that the fibrous structure is more concentrated than structure of FIG. 2A due to the aforementioned cold pressing. Since the rolling reduction is 60% or greater, the density of the structure (i.e. the number of grains included in a unit length orthogonal to length of the grains) is twice or more. Work hardening has progressed in this portion, resulting in hardness of 550 Hv or greater. FIG. 2C shows that the fibrous structure is crushed through press working as described above, extending horizontally. The density of the structure is half or less of that in FIG. 2A. FIG. 2D shows that grains are spread along the width of the paddle-shaped end and are crushed and extended along the thickness of the paddle-shaped end at the same time.

The rolling reduction (%) is defined by the following equation.

$$[(d-t)/d] \times 100\%$$

d: diameter of the work 10 before pressing
t: thickness of the end 10b after pressing Afterwards, the work 10 is loaded into a grinder in which the shape of the end thereof is adjusted and a cutting blade is formed at the same time.

FIGS. 3A to 3D show a work with cutting blades formed; wherein FIG. 3A is a plan view thereof, FIG. 3B shows the shape of the right end surface thereof, FIG. 3C shows a cross section of the work of FIG. 3A cut along the line E-E, and FIG. 3D is an enlarged view showing that the end 10b of the work is carved into a main body 10c of a medical knife.

Cutting blades 10d are formed at the periphery of the end 10b by grinding the end 10b with a grindstone or the like and then carving the resulting adjusted end shape into the main body 10c of the medical knife. While with this embodiment all surfaces of the main body of the medical knife are ground into an adjusted shape, a part of surfaces of the end 10b may be left intact without being ground. Grinding is performed while cooling with grinding oil or the like, preventing decrease in hardness as the surrounding temperature rises.

As shown in FIG. 3D, it is preferable to form the cutting blades 10d at positions away from around a centerline "a" along the thickness of the end 10b. The hardness of the central area along the thickness thereof is low, and impurities tend to concentrate at the center along the thickness. If cutting blades 10d are formed at the center along the thickness and then finished through electrolytic polishing or chemical polishing, the blades would chip and lose desired sharpness because impurities tend to be easily etched.

A medical knife formed in such a manner is fixed to a shaft not shown in the figures and used for medical treatment.

Figures 4, 5:
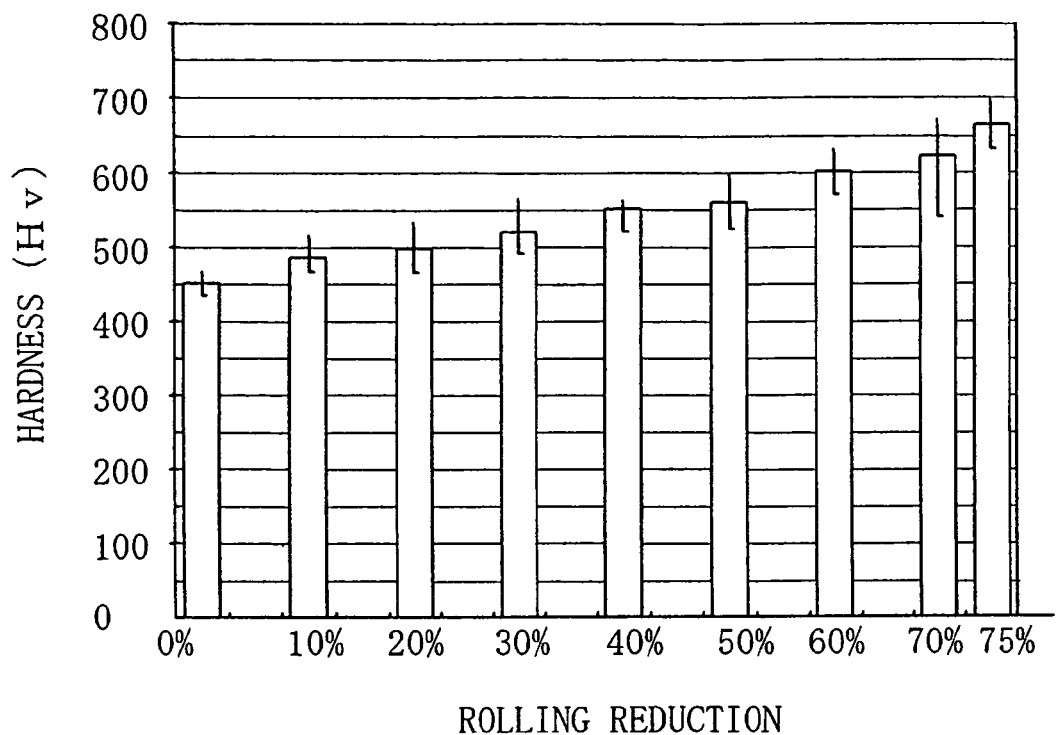
FIG. 4 is a graph showing a relationship between rolling reduction due to press working and change in hardness due to work hardening.
FIG. 5 is a table showing the results of doctors using medical knives, which are fabricated with a variety of rolling reductions.

FIG. 4 shows a relationship between rolling reduction due to press working and change in hardness due to work hardening. With this embodiment, a wire rod of the SUS 302 described above having a diameter of 1 mm is used as the work 10. The vertical axis of FIG. 4 represents vickers hardness (Hv) while the horizontal axis represents rolling reduction (%). Six works are subjected to press working at a variety of rolling reductions, and hardness thereof is then measured; the averages are shown in a bar graph. Each of lines on respective bars denotes the maximum and the minimum value of six measurements. As shown in FIG. 4, as the rolling reduction rises, the hardness also rises linearly. When the rolling reduction is 60%, the minimum value of the hardness is 550 Hv or greater, and the average reaches 600 Hv. Note that a press working process at a rolling reduction of 75% or greater cannot be executed with the pressing machine we have used.

FIG. 5 is a table showing the results of doctors using medical knives for ophthalmic surgery, which are fabricated at a variety of rolling reductions.

According to this table, cutting blades formed at a rolling reduction of 0%, namely, directly formed in the wire rod, have hardness of 434 Hv to 467 Hv, which is below the necessary hardness for medical knives, and thus all doctors A to D have evaluated them with X (not enough). Afterwards, as the rolling reduction rises, the hardness also rises, and thus the evaluation by the doctors rises from X (not enough) to Δ (good). When the rolling reduction is 60%, the hardness is 571 Hv to 632 Hv, and thus three of four doctors have evaluated them with ○ (excellent) and only one has evaluated them with Δ (good). Furthermore, when the rolling reduction is 75%, the hardness is 634 Hv to 697 Hv, and thus all of the doctors have evaluated them with ○ (excellent). Note that while with this embodiment the results from using medical knives for ophthalmic surgery are collected, the same results as those from using medical knives for other medical purposes, cerebral surgery, blood vessels or the like may be expected.

Therefore, it is apparent that practical medical knives can be provided as long as the rolling reduction is 60% or greater, preferably approximately 550 Hv, more preferably 600 Hv or greater.

While the invention has been described with reference to particular example embodiments, further modifications and improvements which will occur to those skilled in the art, may be made within the purview of the appended claims, without departing from the scope of the invention in its broader aspect.

What is claimed is:

1. A medical knife, comprising:
   a knife body having a round wire rod shaped base and a flat-shaped end with two flat surfaces and at least an angled surface therebetween and a cutting blade formed on an edge of the angled surface which forms a periphery of the flat-shaped end; and
   wherein said flat-shaped end has a Vickers Hardness of at least 550 Hv and said round wire rod shaped base has a Vickers Hardness of 434-467 Hv; and
   wherein said medical knife comprises stainless steel with at least 50% martensitic crystalline structure and the remainder being austenitic crystalline structure.

2. The medical knife according to claim 1, wherein at least one of the martensitic crystalline structure and the austenitic crystalline structure comprises crystal grains having a size of approximately 30-40 μm along a width of the cutting blade.

3. The medical knife according to claim 1, wherein said stainless steel comprises a SUS 302 Type B stainless steel having a carbon content of 0.08% to 0.15% in mass %.

4. The medical knife according to claim 1, wherein said two flat surfaces are parallel to each other.

5. A medical knife, comprising:
a knife body having a flat-shaped end having a hardness of at least 550 Hv and a round wire rod shaped base having a hardness of 434-467 Hv; and
a cutting blade disposed in a region of the flat-shaped end;
said medical knife being formed by a process comprising the steps of:
forming a wire rod by drawing austenitic stainless steel so that the wire rod has a hardness of 434-467 Hv before a cold pressing step or a press cutting step; and
cold pressing or press cutting an end of the wire rod to form the flat-shaped end so that said flat-shaped end has a hardness of at least 550 Hv.

6. The medical knife according to claim 5,
wherein said step of forming the cutting blade is by grinding the periphery of said flat-shaped end with a grindstone.

7. The medical knife according to claim 6,
wherein said cutting blade is polished by electrolytic polishing.

8. The medical knife according to claim 6,
wherein said cutting blade is polished by chemical polishing.

9. The medical knife according to claim 5,
wherein said rod of austenitic stainless steel is given at least 50% martensitic crystalline structure and a remainder of austenitic crystalline structure by repeated wire drawing and solution heat treatment.

10. The medical knife according to claim 5,
wherein said rod of austenitic stainless steel has a carbon content of 0.08% to 0.15% in mass %.

11. A medical knife, comprising:
a knife body having a round wire rod shaped base and a flat-shaped end with two flat surfaces and at least an angled surface therebetween and a cutting blade formed on an edge of the angled surface which forms a periphery of the flat-shaped end,
the flat-shaped end having a Vickers Hardness of at least 550 Hv and the round wire rod shaped base having a Vickers Hardness of 434-467 Hv, and
comprising stainless steel with at least 50% martensitic crystalline structure and the remainder comprising austenitic crystalline structure, said medical knife being formed by a process comprising the steps of:
repeating solution heat treating and wire drawing of a wire rod so that the wire rod has increased in Vickers hardness to 434-467 Hv before a cold pressing step or a press cutting step;
cutting the wire rod into a predetermined length;
cold pressing or press cutting one end of the wire rod to form the flat-shaped end having a Vickers Hardness of at least 550 Hv; and
forming the cutting blade by grinding the periphery of the flat-shaped end between the two flat surfaces.

12. The medical knife according to claim 11, wherein the stainless steel is a SUS 302 Type B stainless steel having a carbon content of 0.08% to 0.15% in mass %.

13. The medical knife according to claim 11, wherein said two flat surfaces are parallel to each other.

* * * * *